United States Patent
Pratt et al.

(10) Patent No.: US 10,478,536 B2
(45) Date of Patent: Nov. 19, 2019

(54) THERAPY APPARATUS WITH INTEGRATED FLUID CONDUCTORS AND NOISE ATTENUATION

(71) Applicant: KCI Licensing, Inc., San Antonio, TX (US)

(72) Inventors: Benjamin Andrew Pratt, Poole (GB); James Killingworth Seddon, Ferndown (GB); Christopher Brian Locke, Bournemouth (GB); David Mercer, Bournemouth (GB); Loren Francis, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 697 days.

(21) Appl. No.: 14/849,321

(22) Filed: Sep. 9, 2015

(65) Prior Publication Data

US 2016/0067392 A1    Mar. 10, 2016

Related U.S. Application Data

(60) Provisional application No. 62/048,638, filed on Sep. 10, 2014.

(51) Int. Cl.
*A61M 1/00* (2006.01)
*B29L 31/00* (2006.01)

(52) U.S. Cl.
CPC .......... *A61M 1/0088* (2013.01); *A61M 1/009* (2014.02); *A61M 1/0001* (2013.01); *A61M 2207/00* (2013.01); *B29L 2031/753* (2013.01)

(58) Field of Classification Search
CPC .............. A61M 1/0001; A61M 1/0003; A61M 1/0023; A61M 1/0058; A61M 1/0066;
(Continued)

(56) References Cited

U.S. PATENT DOCUMENTS 1,355,846 A    10/1920   Rannells
2,547,758 A    4/1951    Kelling
(Continued)

FOREIGN PATENT DOCUMENTS

AU    550575 B2    3/1986
AU    745271 B2    3/2002
(Continued)

OTHER PUBLICATIONS

"By Design, Part design 107: Draft angles", Injection Molding, Materials; Glenn Beall, Jan. 31, 2000 (Year: 2000).*
(Continued)

*Primary Examiner* — Benjamin J Klein

(57) ABSTRACT

In one example embodiment, an apparatus may include a panel with integrated fluid channels, wherein the panel and the fluid channel consist only of surfaces that can be manufactured with a straight-pull mold. A port may also be integrated into the panel to facilitate coupling the fluid channel to pneumatic components in an assembly. A seal may be secured to the panel over the fluid channel to form an integrated fluid conductor. The seal is preferably an adhesive label that can also be used for product labeling. Such an apparatus may be used in a control unit of a therapy system, employing several integrated fluid conductors. A method of manufacturing may include molding a panel, wherein the mold forms a channel integral to the panel. The panel and the channel preferably consist of surfaces that can be molded with a straight-pull mold.

4 Claims, 11 Drawing Sheets

(58) Field of Classification Search
CPC ............. A61M 1/0088; A61M 2207/00; B29L 231/753
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,888,331 A * | 6/1975 | Wang | F01N 1/06 181/253 |
| 4,080,970 A | 3/1978 | Miller | |
| 4,096,853 A | 6/1978 | Weigand | |
| 4,139,004 A | 2/1979 | Gonzalez, Jr. | |
| 4,161,264 A * | 7/1979 | Malmgren | A61M 1/1656 222/135 |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,798,580 A * | 1/1989 | DeMeo | A61M 1/0058 417/476 |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,950,235 A * | 8/1990 | Slate | A61M 5/16831 128/DIG. 13 |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,464,391 A * | 11/1995 | DeVale | A61M 3/0258 128/DIG. 12 |
| 5,466,229 A * | 11/1995 | Elson | A61M 1/0023 604/257 |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,746,719 A * | 5/1998 | Farra | A61M 1/0058 128/DIG. 12 |
| 6,071,267 A | 6/2000 | Zamierowski | |
| 6,135,116 A | 10/2000 | Vogel et al. | |
| 6,145,160 A * | 11/2000 | Buss | A47L 5/362 15/323 |
| 6,241,747 B1 | 6/2001 | Ruff | |
| 6,261,065 B1 * | 7/2001 | Nayak | F04B 49/06 417/53 |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,563,248 B2 * | 7/2009 | Smisson, III | A61M 1/0281 604/113 |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0198503 A1 * | 12/2002 | Risk, Jr. | A61M 1/0058 604/315 |
| 2002/0198504 A1 * | 12/2002 | Risk, Jr. | A61M 1/0058 604/318 |
| 2007/0016152 A1 * | 1/2007 | Karpowicz | A61M 1/0001 604/326 |
| 2007/0135779 A1 * | 6/2007 | Lalomia | A61M 1/0005 604/319 |

(56) References Cited

U.S. PATENT DOCUMENTS

| | | | |
|---|---|---|---|
| 2007/0167927 A1* | 7/2007 | Hunt | A61M 1/0023 604/313 |
| 2009/0030383 A1* | 1/2009 | Larsen | A61M 1/0031 604/290 |
| 2009/0157016 A1* | 6/2009 | Adahan | A61M 1/0001 604/290 |
| 2009/0264837 A1* | 10/2009 | Adahan | A61M 1/0031 604/290 |
| 2009/0326488 A1* | 12/2009 | Budig | A61M 1/0001 604/313 |
| 2010/0185165 A1* | 7/2010 | Middleton | A61M 1/0031 604/319 |
| 2010/0312202 A1* | 12/2010 | Henley | A61M 1/0088 604/319 |
| 2011/0051136 A1* | 3/2011 | Milton | A61M 1/0058 356/338 |
| 2011/0288512 A1* | 11/2011 | Locke | A61M 1/0066 604/319 |
| 2012/0136325 A1* | 5/2012 | Allen | A61M 1/0031 604/319 |
| 2013/0110058 A1* | 5/2013 | Adie | A61M 1/0031 604/319 |
| 2014/0163487 A1* | 6/2014 | Tout | A61M 3/0258 604/305 |
| 2014/0163491 A1 | 6/2014 | Schuessler et al. | |
| 2014/0309619 A1* | 10/2014 | Agarwal | A61M 5/158 604/506 |
| 2015/0080788 A1 | 3/2015 | Blott et al. | |
| 2015/0224237 A1* | 8/2015 | Reasoner | A61M 1/0023 604/320 |
| 2016/0038658 A1* | 2/2016 | Chien | A61M 1/0011 604/319 |
| 2016/0166781 A1* | 6/2016 | Sarangapani | A61M 13/003 604/23 |
| 2016/0250398 A1* | 9/2016 | Barr | A61M 1/0023 604/319 |
| 2017/0274124 A1* | 9/2017 | Hartwell | A61M 1/0031 |
| 2017/0340784 A1* | 11/2017 | Hall | A61M 1/0058 |
| 2018/0001000 A1* | 1/2018 | Herwig | A61M 1/0007 |
| 2018/0111121 A1* | 4/2018 | Amshey | B01L 3/502715 |

FOREIGN PATENT DOCUMENTS

| | | |
|---|---|---|
| AU | 755496 B2 | 12/2002 |
| CA | 2005436 A1 | 6/1990 |
| CN | 1437488 A | 8/2003 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | H07208144 A | 8/1995 |
| JP | 2006234600 A | 9/2006 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 9818507 A1 | 5/1998 |
| WO | 99/13793 A1 | 3/1999 |
| WO | 0118395 A1 | 3/2001 |
| WO | 2010075178 A2 | 7/2010 |
| WO | 2014082003 A1 | 5/2014 |

OTHER PUBLICATIONS

International Search Report and Written Opinion for corresponding PCT Application No. PCT/US2015/049240 dated Mar. 2, 2016.

Louis C. Argenta, MD and Michael J. Morykwas, PHD; Vacuum-Assisted Closure: A New Method for Wound Control and Treatment: Clinical Experience; Annals of Plastic Surgery.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

(56) References Cited

OTHER PUBLICATIONS

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinović, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

Chinese First Office Action for Corresponding Application No. 201580054313, dated Dec. 18, 2018.

Japanese Notice of Rejection corresponding to Application No. 2017-513071, dated Aug. 13, 2019.

\* cited by examiner

THERAPY APPARATUS WITH INTEGRATED FLUID CONDUCTORS AND NOISE ATTENUATION

RELATED APPLICATION

This present invention claims the benefit, under 35 USC § 119(e), of the filing of U.S. Provisional Patent Application Ser. No. 62/048,638, entitled "THERAPY APPARATUS WITH INTEGRATED FLUID CONDUCTORS AND NOISE ATTENUATION," filed Sep. 10, 2014, which is incorporated herein by reference for all purposes.

TECHNICAL FIELD

The invention set forth in the appended claims relates generally to tissue treatment systems and more particularly, but without limitation, to apparatuses with integrated fluid conductors and noise attenuation, and methods of manufacturing and using the same.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of a wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

BRIEF SUMMARY

New and useful systems, apparatuses, and methods related to tissue treatment are set forth in the appended claims. Illustrative embodiments are also provided to enable a person skilled in the art to make and use the claimed subject matter. For example, an apparatus is described herein that may include a panel with integrated fluid channels, wherein the panel and the fluid channel consist only of surfaces that can be manufactured with a straight-pull mold. A port may also be integrated into the panel and fluidly coupled to the fluid channel to facilitate coupling the fluid channel to pneumatic components in an assembly incorporating the panel. In more particular embodiments, a seal may be secured to the panel over the fluid channel to form an integrated fluid conductor. The seal is preferably an adhesive label that can also be used for product labeling.

Such an apparatus may be particularly advantageous for use in a control unit of a negative-pressure therapy system, wherein such an apparatus may employ several such integrated fluid conductors coupled to a pump and other pneumatic components. For example, some embodiments of a therapy apparatus may include a housing comprising a panel with integrated fluid conductors. Negative pressure produced by a pump can be delivered to a dressing via a first integrated fluid conductor. Moreover, in some embodiments, a second integrated fluid conductor may fluidly couple exhaust from the pump to an expansion chamber to attenuate exhaust noise from the pump. In some example embodiments, a baffle may be disposed in the expansion chamber to further attenuate noise. Additionally or alternatively, sound absorbing foam may also be disposed in the expansion chamber. Alternatively, other example embodiments may include an integrated fluid conductor configured to direct exhaust fluid along a serpentine path to attenuate noise.

In some embodiments, an apparatus may have a first housing and a second housing. A panel may be integral with or otherwise coupled to the second housing, and the panel may be configured with an integrated fluid channel disposed around a perimeter of the panel. Fasteners may be disposed through the panel within the perimeter defined by the integrated fluid conductor, and the fasteners may couple the second housing to the first housing. A seal may be secured to the panel over the fasteners and the integrated fluid channel. The integrated fluid conductor formed by the seal and the integrated fluid channel may fluidly couple a negative-pressure source to a negative-pressure outlet, such as a canister port. Removing the seal in such embodiments to gain access to the fasteners may break the pneumatic circuit between the negative-pressure source and the negative-pressure outlet, interfering with operation of the device. Accordingly, such embodiments may be advantageous for preventing tampering or other unauthorized disassembly.

Methods of manufacturing an apparatus are also described herein. Some example embodiments include molding a panel, wherein the mold forms a channel integral to the panel. The panel and the channel preferably consist of surfaces that can be molded with a straight-pull mold. A seal, such as an adhesive label, may be applied to the panel over the channel to form an integrated fluid conductor. In some embodiments, the mold further forms a port integral to the panel, wherein the port is fluidly coupled to the channel and configured to couple the channel to a pneumatic component. Preferably, the panel, the channel, and other features of the panel are substantially free of undercuts and overhangs.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
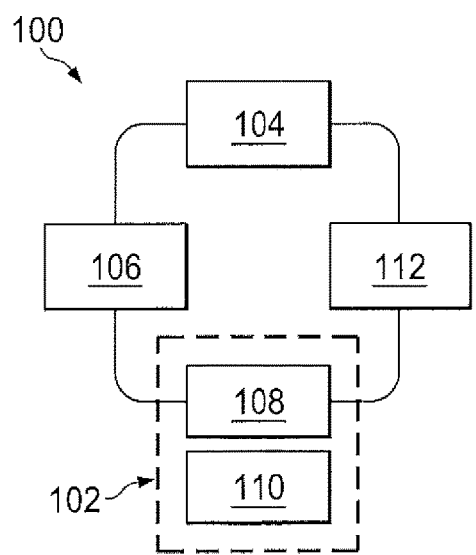
FIG. 1 is a functional block diagram of an example embodiment of a therapy system that can provide negative-pressure therapy in accordance with this specification.

FIG. 1 is a simplified functional block diagram of an example embodiment of a therapy system 100 in accordance with this specification. The negative-pressure therapy system 100 may include a dressing and a negative-pressure source. For example, a dressing 102 may be fluidly coupled to a negative-pressure source 104, as illustrated in FIG. 1. A regulator or controller, such as a regulator 106, may also be fluidly coupled to the dressing 102 and the negative-pressure source 104. A dressing generally includes a cover and a tissue interface. The dressing 102, for example, may include a cover 108 and a tissue interface 110. The therapy system 100 may also include a fluid container, such as a container 112, coupled to the dressing 102 and to the negative-pressure source 104.

In general, components of the therapy system 100 may be coupled directly or indirectly. For example, the negative-pressure source 104 may be directly coupled to the regulator 106 and indirectly coupled to the dressing 102 through the regulator 106. In some embodiments, components may be coupled by virtue of physical proximity, being integral to a single structure, or being formed from the same piece of material. Coupling may also include mechanical, thermal, electrical, or chemical coupling (such as a chemical bond) in some contexts.

Components may also be fluidly coupled to each other to provide a path for transferring fluids (i.e., liquid and/or gas) between the components. In some embodiments, for example, components may be fluidly coupled through a fluid conductor. A "fluid conductor," as used herein, broadly refers to a tube, pipe, hose, conduit, or other structure with one or more lumina adapted to convey a fluid between two ends. A tube, for example, is typically an elongated, cylindrical structure with some flexibility, but the geometry and rigidity may vary.

In operation, the tissue interface 110 may be placed within, over, on, or otherwise proximate to a tissue site. The cover 108 may be placed over the tissue interface 110 and sealed to tissue near the tissue site. For example, the cover 108 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 110 in the sealed therapeutic environment can induce macrostrain and microstrain in the tissue site, as well as remove exudates and other fluids from the tissue site, which can be collected in container 112 and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, in the context of a system for negative-pressure therapy, the term "downstream" typically implies something in a fluid path relatively closer to a negative-pressure source, and conversely, the term "upstream" implies something relatively further away from a negative-pressure source. Similarly, it may be convenient to describe certain features in terms of fluid "inlet" or "outlet" in such a frame of reference. This orientation is generally presumed for purposes of describing various features and components of negative-pressure therapy systems herein. However, the fluid path may also be reversed in some applications (such as by substituting a positive-pressure source for a negative-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures, Similarly, references to increases in negative pressure typically refer to a decrease in absolute pressure, while decreases in negative pressure typically refer to an increase in absolute pressure.

A negative-pressure source, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

The tissue interface 110 can be generally adapted to contact a tissue site. The tissue interface 110 may be partially or fully in contact with the tissue site. If the tissue site is a wound, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites.

In some embodiments, the tissue interface 110 may be a manifold. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In an example in which the tissue interface 110 may be made from a hydrophilic material, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 110 may further promote granulation at a tissue site when pressure within the sealed therapeutic environment is reduced. For example, any or all of the surfaces of the tissue interface 110 may have an uneven, coarse, or jagged profile that can induce microstrains and stresses at a tissue site if negative pressure is applied through the tissue interface 110.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 108 may provide a bacterial barrier and protection from physical trauma. The cover 108 may also be constructed from a material that can reduce evaporative losses and provide a fluid barrier between two components or two environments, such as between a therapeutic environment and a local external environment. The cover 108 may be, for example, an elastomeric film or membrane that can be sealed around a tissue site to maintain a negative pressure at the tissue site for a given negative-pressure source. In some example embodiments, the cover 108 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 108 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 108 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

Figure 2:
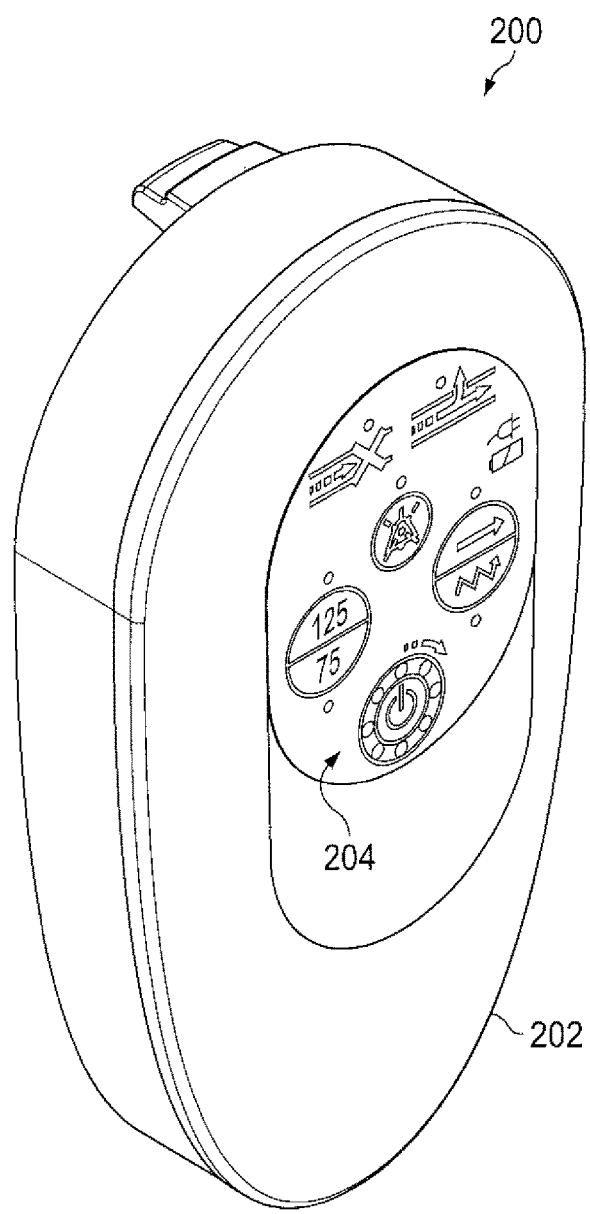
FIG. 2 is a perspective view of a control unit, illustrating additional details that may be associated with some example embodiments of the example therapy system of FIG. 1.

FIG. 2 is a perspective view of a control unit 200, illustrating additional details that may be associated with some example embodiments of the therapy system 100. The control unit 200 may provide a housing 202 for the negative pressure source 104, and may also provide a user interface, such as the interface 204. In some embodiments, the control unit 200 may also integrate other components, such as the container 112, for example.

Figure 3:
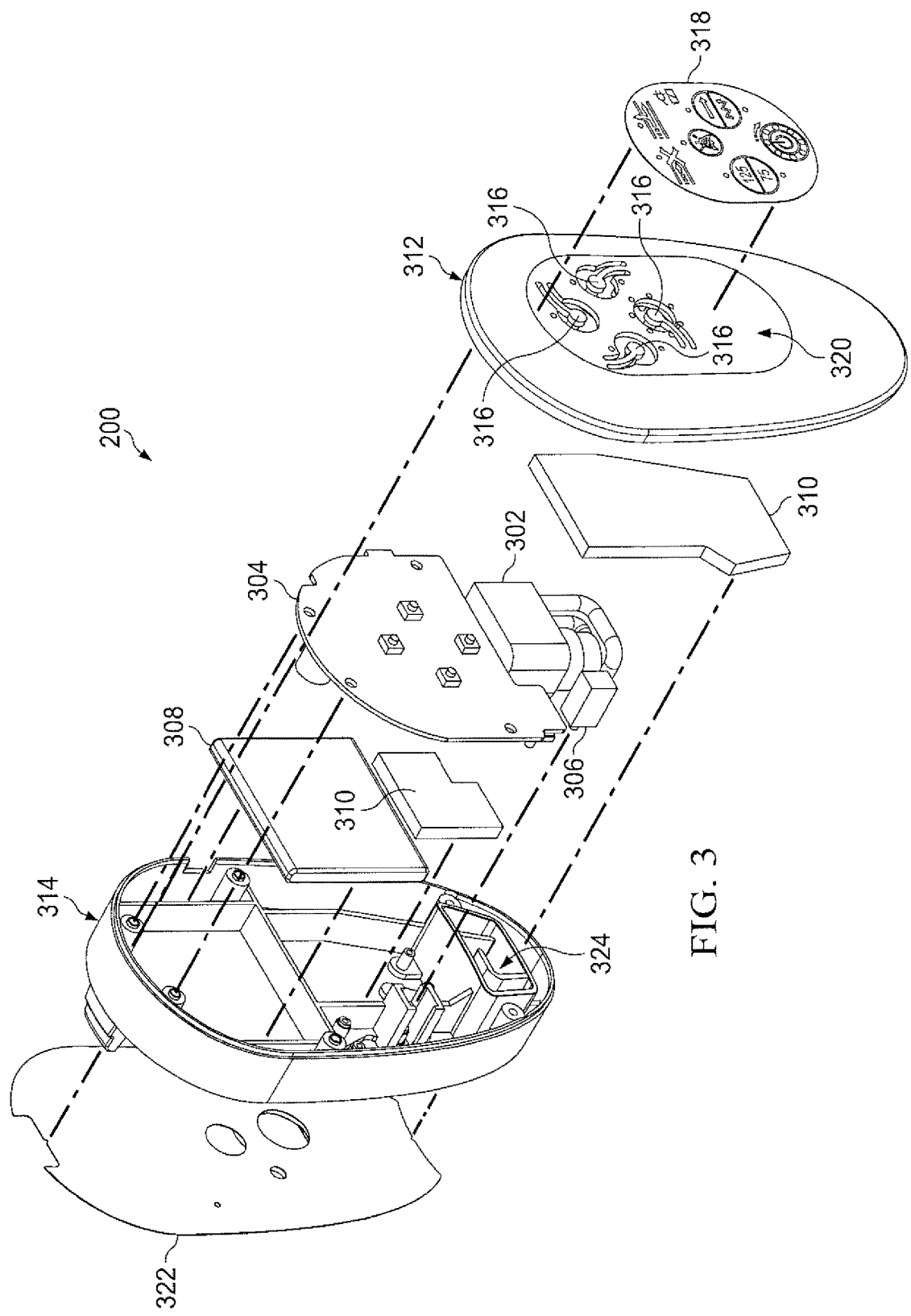
FIG. 3 is an exploded view of the control unit of FIG. 2, illustrating additional details that may be associated with some embodiments.

FIG. 3 is an exploded view of the control unit 200, illustrating additional details that may be associated with some embodiments. As illustrated in the example embodiment of FIG. 3, the control unit 200 may include a vacuum pump 302, a printed wiring assembly 304, a valve 306, a power source such as a battery 308, and a mounting foam 310. The vacuum pump 302 is an example embodiment of the negative pressure source 104 in FIG. 1. As illustrated in FIG. 3, some embodiments of the housing 202 may comprise a first housing 312 and a second housing 314, which may be coupled to enclose the vacuum pump 302, the printed wiring assembly 304, the valve 306, the battery 308, and the mounting foam 310. The first housing 312 may include controls 316 and an interface overlay 318, which may be attached to a control panel 320 over the controls 316 to form the interface 204 in some embodiments. The control unit 200 may also include a seal 322. An expansion chamber 324 may also be coupled to or otherwise disposed in the second housing 314 in some embodiments of the control unit 200.

The mounting foam 310 is preferably a low-density foam, which can positioned between the vacuum pump 302 and the housing 202. Illustrative examples of the mounting foam 310 include a melamine, polyester polyurethane, or impregnated polyether foam with a density approximately in the range of 10-100 kilograms per cubic meter, The mounting foam 310 may have an adhesive backing or may be pre-bonded to the first housing 312 and the second housing 314 in some embodiments to simplify assembly.

The seal 322 preferably comprises a material that is relatively pliable and impermeable to fluid. For example, the seal 322 may be manufactured from a non-porous polyester film, preferably having a thickness between 0.1 millimeter and 0.2 millimeter. The seal 322 also preferably comprises an adhesive or other suitable means for attaching the seal 322 to the second housing 314. For example, the seal 322 may include an acrylic adhesive applied to one side, preferably having a thickness of about 0.15 millimeters. In some embodiments, the seal 322 may also be an adhesive label or integrated with product labeling.

The expansion chamber 324 is preferably sealed to retain any condensation from humid air flowing through the expansion chamber in operation. For example, the mounting foam 310 may be compressed against the upper edges of the expansion chamber 324 to fluidly isolate the interior of the expansion chamber 324 from other components, particularly components that may be adversely affected by moisture.

Figure 4:
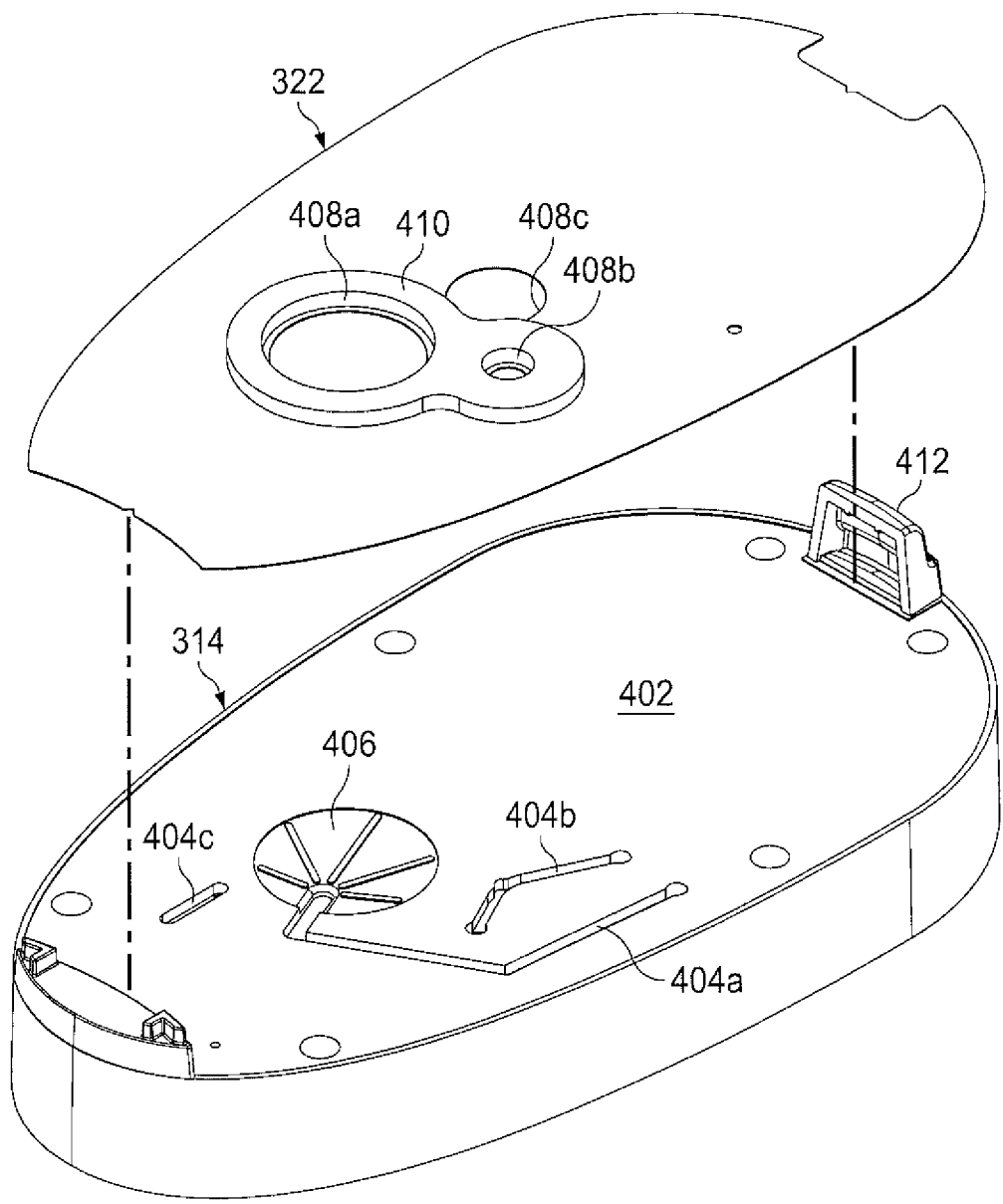
FIG. 4 is an exploded view of a housing and a seal that may be associated with some embodiments of the control unit of FIG. 2.

FIG. 4 is an exploded view of the second housing 314 and the seal 322. As shown in FIG. 4, some embodiments of the second housing 314 may include one or more fluid channels. For example, in the embodiment illustrated in FIG. 4, the second housing 314 may comprise a panel 402, and fluid channels 404a-404c may be integrated into the panel 402. In some embodiments, the fluid channels 404a-404c may be open channels, as shown in FIG. 4. Such open channels may, for example, be formed as a groove, furrow, cut, depression, or gutter in the panel 402. In some embodiments, the fluid channels 404a-404c may have rectangular, semi-circular, or trapezoidal cross-sections, for example. A canister port 406 may also be coupled to the second housing 314. For example, as shown in the example embodiment of FIG. 4, the canister port 406 may be integral to the panel 402, and may also be fluidly coupled to one or more of the fluid channels, such as the fluid channel 404a. The seal 322 may also have apertures such as apertures 408a-408c, which can be aligned with various features in the second housing 314. In some embodiments, for example, the aperture 408a may be aligned with the canister port 406, and the aperture 408b may be aligned and fluidly coupled with a terminus or other portion of the fluid channel 404b. A gasket 410 may also be coupled to the seal 322 around the aperture 408a, the aperture 408b, the aperture 408c, or any combination thereof. The second housing 314 may also include a canister latch 412 to facilitate fastening the second housing 314 to a canister.

Figure 5:
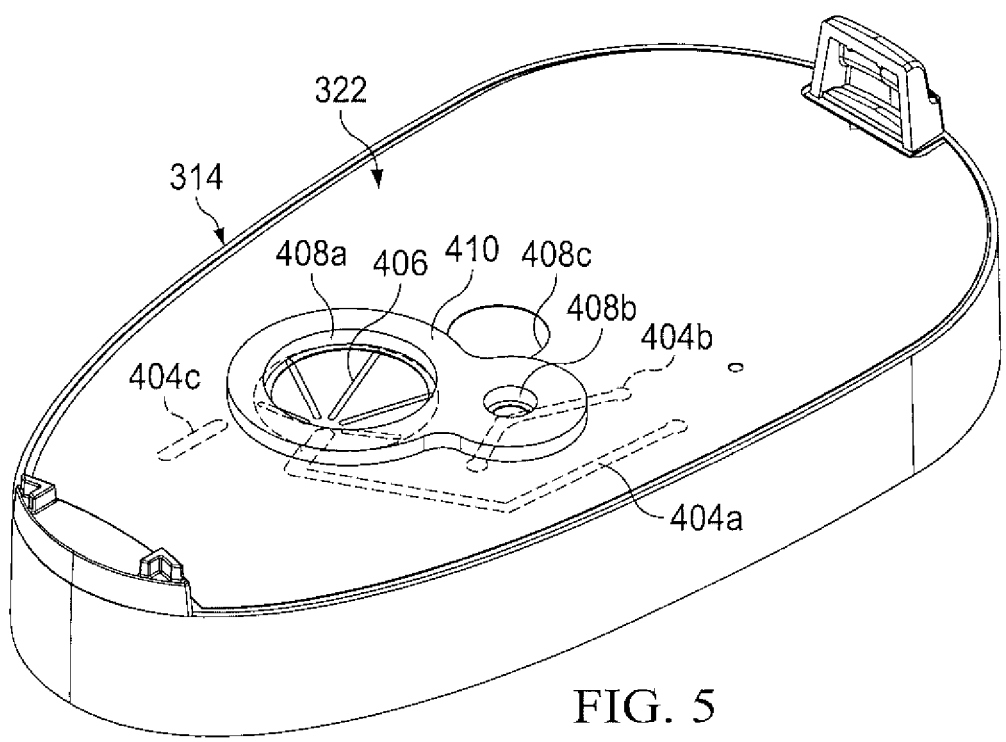
FIG. 5 is a perspective view of the assembly of the housing and the seal of FIG. 4.

FIG. 5 is a perspective view of the second housing 314 assembled with the seal 322. Assembled as shown in the example embodiment of FIG. 5, the seal 322 is attached to the panel 402 and covers the fluid channels 404a-404c. In some embodiments, the seal 322 may not cover all of the fluid channels 404a-404c. Rather, in some example embodiments, the seal 322 may only cover one or two of the fluid channels 404a-404c, and additional seals may be attached to the panel 402 to cover individual fluid channels. The seal 322 preferably provides a margin of at least 5 millimeters around the perimeter of a channel, Although the seal 322 may be transparent in some embodiments, the fluid channels 404a-404c are shown as hidden lines in FIG. 5. FIG. 5 also illustrates the alignment of aperture 408a with the canister port 406 in this example embodiment, and further illustrates the alignment of the aperture 408b with an intermediate portion of the fluid channel 404b.

Figure 6:
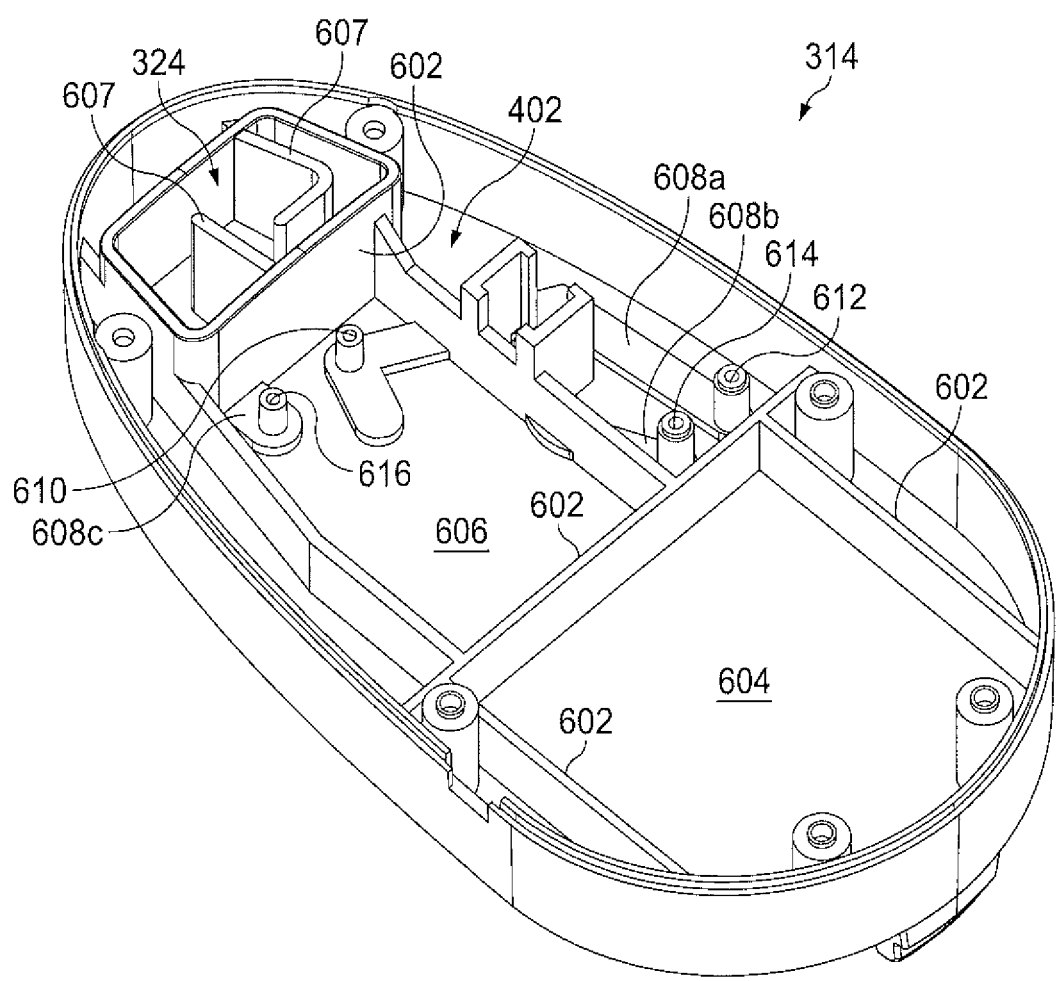
FIG. 6 is a perspective view of the housing of FIG. 4 from the opposite side of FIG. 5, illustrating additional details that may be associated with some embodiments.

FIG. 6 is a perspective view of the second housing 314 from the opposite side of FIG. 5, illustrating additional details that may be associated with some embodiments. For example, the second housing 314 may include partitions 602 that partition the second housing 314 into compartments, such as a battery compartment 604 and a pump compartment 606.

One or more of the partitions 602 may also form at least part of the expansion chamber 324, as illustrated in the example embodiment of FIG. 6. Also as illustrated in the example of FIG. 6, some embodiments of the expansion chamber 324 may include one or more baffles 607. The baffles 607 may be a panel, plate, wall or other partition, for example, disposed in the expansion chamber 324 to direct the flow of fluid or otherwise define a fluid path. The baffles 607 are preferably substantially impervious to fluid, and may be configured to increase sound attenuation by reflecting sound waves and directing fluid along a tortuous or serpentine path, for example.

One or more channel extensions may also be integrated into the panel 402. For example, channel extensions 608a-608c may be ridges or ribs that track the fluid channels 404a-404c in the panel 402, which can provide additional depth to the fluid channels. Moreover, at least one fluid port may also be coupled to the panel 402. For example, as shown in FIG. 6, a channel port 610 may be integrated into the channel extension 608a. A fluid port, such as the channel port 610, may include either a male or female connector. For example, the channel port 610 illustrated in the example embodiment of FIG. 6 may include a single male fitting, which generally comprises a protruding body such as a bolt, post, or mounting boss adapted for insertion into a compatible female connector, receptacle, or lumen. The example embodiment of FIG. 6 also includes a channel port 612, a channel port 614, and a channel port 616, which can include features similar or analogous to the channel port 610.

Figure 7:
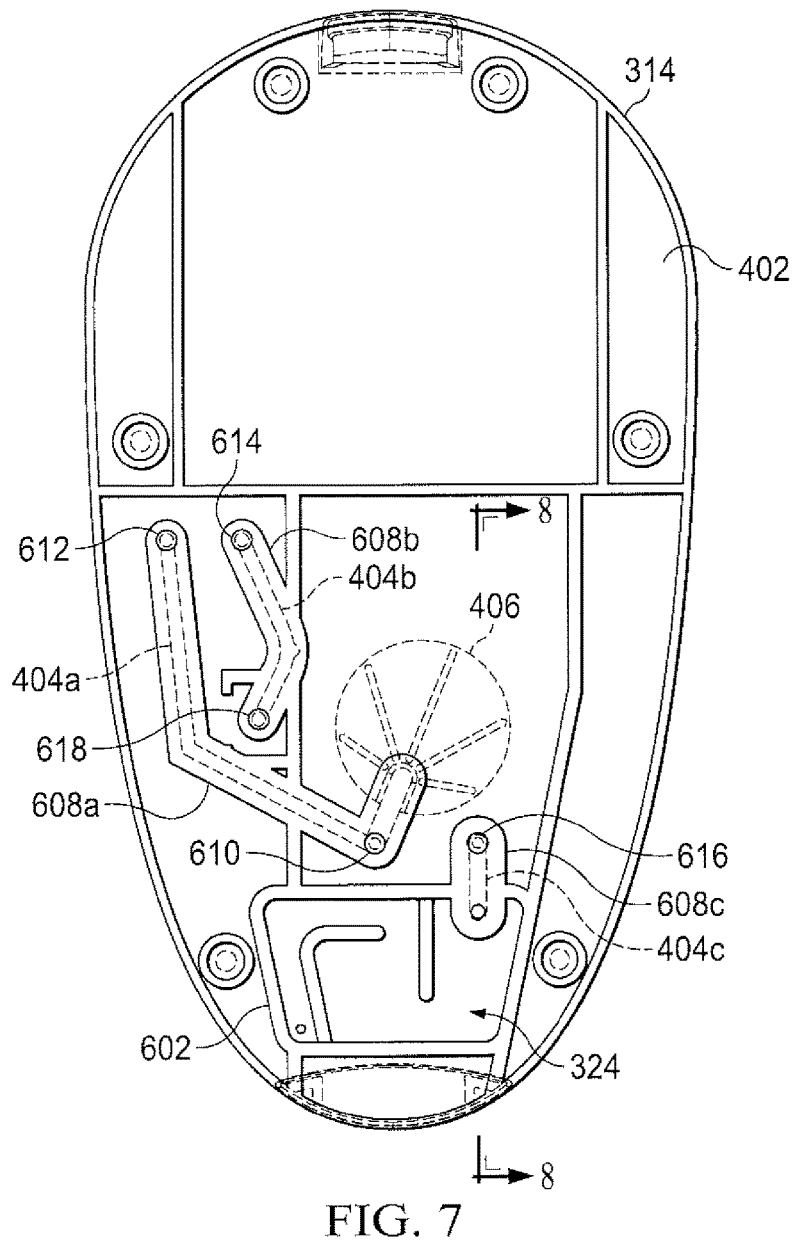
FIG. 7 is a plan view of the housing of FIG. 6, illustrating additional details that may be associated with some example embodiments.

FIG. 7 is a plan view of the second housing 314 of FIG. 6, illustrating additional details that may be associated with some example embodiments. For example, FIG. 7 further illustrates a relationship between the fluid channels 404a-404c, which are shown as hidden lines in FIG. 7, and the channel extensions 608a-608c. More specifically, in the example embodiment of FIG. 7, a longitudinal axis of each of the channel extensions 608a-608c can be aligned with a respective longitudinal axis of the fluid channels 404a-404c.

FIG. 7 also illustrates example embodiments of the channel port 610, the channel port 612, the channel port 614, and the channel port 616. For example, one end of the fluid channel 404a can be fluidly coupled to the canister port 406 and an opposing end of the fluid channel 404a can be fluidly coupled to the channel port 612. In some embodiments, a channel port may be fluidly coupled to each terminus of a fluid channel. For example, as shown in FIG. 7, the channel port 614 can be fluidly coupled to a first terminus of the fluid channel 404b and a channel port 618 may be fluidly coupled to a second terminus of the fluid channel 404b. One or more channel ports may also be fluidly coupled to a fluid channel between each terminus. For example, the channel port 610 may be fluidly coupled to an intermediate point of the fluid channel 404a.

Figure 8:
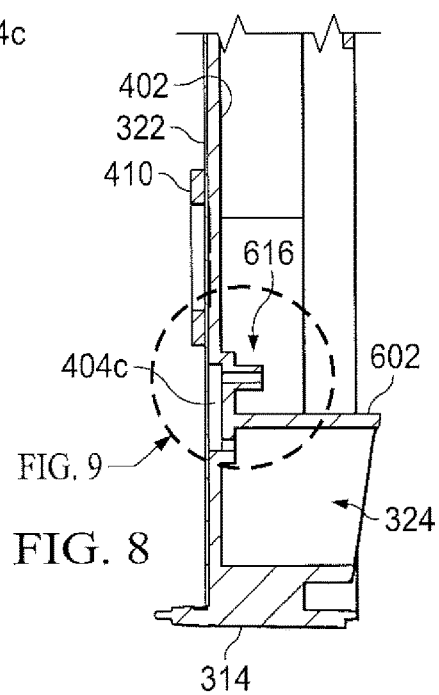
FIG. 8 is a section view of the housing and the seal of FIG. 7 taken along line 8-8.

FIG. 8 is a section view of the second housing 314 and the seal 322 taken along line 8-8 of FIG. 7, illustrating additional details that may be associated with some embodiments. For example, in the example embodiment of FIG. 8, the fluid channel 404c extends across a proximal end of the partition 602. The seal 322 may be secured to the panel 402, as shown in FIG. 8. In this example embodiment, the seal 322 also covers the fluid channel 404c to form an integrated fluid conductor between the expansion chamber 324 and the channel port 616. The seal 322 may also cover other fluid channels, such as the fluid channel 404a, the fluid channel 404b, or both, to form additional fluid conductors in the panel 402. A seal such as the seal 322 preferably covers and seals the fluid channels completely. In operation, a channel is preferably deep enough to ensure that deformation of the seal under negative pressure does not cause the seal to block the channel.

Figure 9:
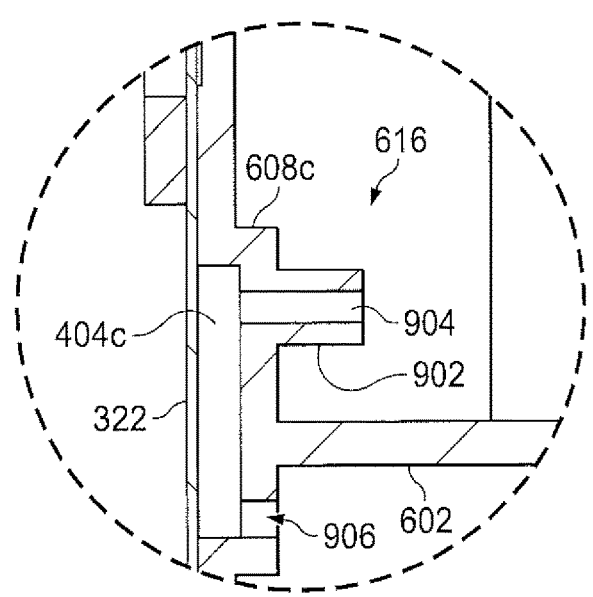
FIG. 9 is a detail view of a section of FIG. 8.

FIG. 9 is a detail view of a section of FIG. 8. As illustrated in FIG. 9, some embodiments of the port 616 may include an alignment post 902 and a fluid conductor, such as a passage 904. The passage 904 may be coupled to the fluid channel 404c, which can be fluidly coupled to the expansion chamber 324 through the fluid channel 404c and a passage 906 in the panel 402. As shown again in FIG. 9, the seal 322 spans the fluid channel 404c in this embodiment to form an enclosed fluid conductor integral to the panel 402.

In some embodiments, the second housing 314 may be manufactured with a molding process, such as injection molding. A mold preferably comprises two blocks machined to jointly provide a cavity having the shape and features of a part. To minimize the cost and efficiency of injection molding, a part preferably consists only of surfaces that allow a mold to be separated with a straight pull on the mold in at least one orientation. For example, an undercut on a part can prevent a straight pull on a mold, or may require a side pull that can increase the complexity and cost of manufacturing.

A part design may be visually inspected to identify undercuts or other features that may interfere with a straight pull mold in a particular orientation. Surface designs can also be analyzed by considering each line in a solid model, to determine if each line is continuous and intersects the part surface profile only at a single beginning and a single ending. An example of an automated geometric analysis of a solid model is described by Lukis et al. in U.S. Pat. No. 8,140,401, incorporated herein by reference. Surfaces can also be characterized by the angle between the surface and the direction of pull, referred to herein as the "parting angle." In this context, the parting angle of a surface is equal to ninety degrees minus the angle between the direction of pull and a line that is normal to the surface and intersects the direction of pull. For example, a surface that is parallel to the direction of pull has a parting angle of zero degrees, and a surface that is perpendicular to the direction of pull and facing the direction of pull has a parting angle of ninety degrees. An undercut may also be characterized by a parting angle. For example, a surface that is perpendicular to the direction of pull but faces away from the direction of pull has a parting angle of negative ninety degrees (ninety degrees minus 180 degrees). Using this convention, an undercut has a parting angle less than zero degrees (a negative parting angle), and a part may be characterized as consisting only of straight-pull surfaces if all of the surfaces have a parting angle that is greater than or equal to zero degrees (a positive parting angle) in at least one orientation.

In some embodiments, the second housing 314 may consist entirely of straight-pull surfaces, which can be manufactured with a straight-pull mold in at least one orientation. For example, in some embodiments the direction of pull may be perpendicular to the panel 402, and the panel 402 (including the fluid channels 404a-404c) may consist of surfaces without overhangs or undercuts, which can be manufactured with a straight-pull mold opened perpendicular to the panel 402. Fluid ports, such as the fluid port 610, and channel extensions, such as the channel extensions 608a-608c, may also be designed without undercuts to facilitate straight-pull injection molding. Although the panel 402 is generally illustrated as integral to the second housing 314, the panel 402 may also be manufactured separately and fastened to the second housing 314 in some embodiments. The first housing 312 and other parts of the control unit 200 may also consist of straight-pull surfaces to reduce manufacturing complexity and cost.

Figure 10:
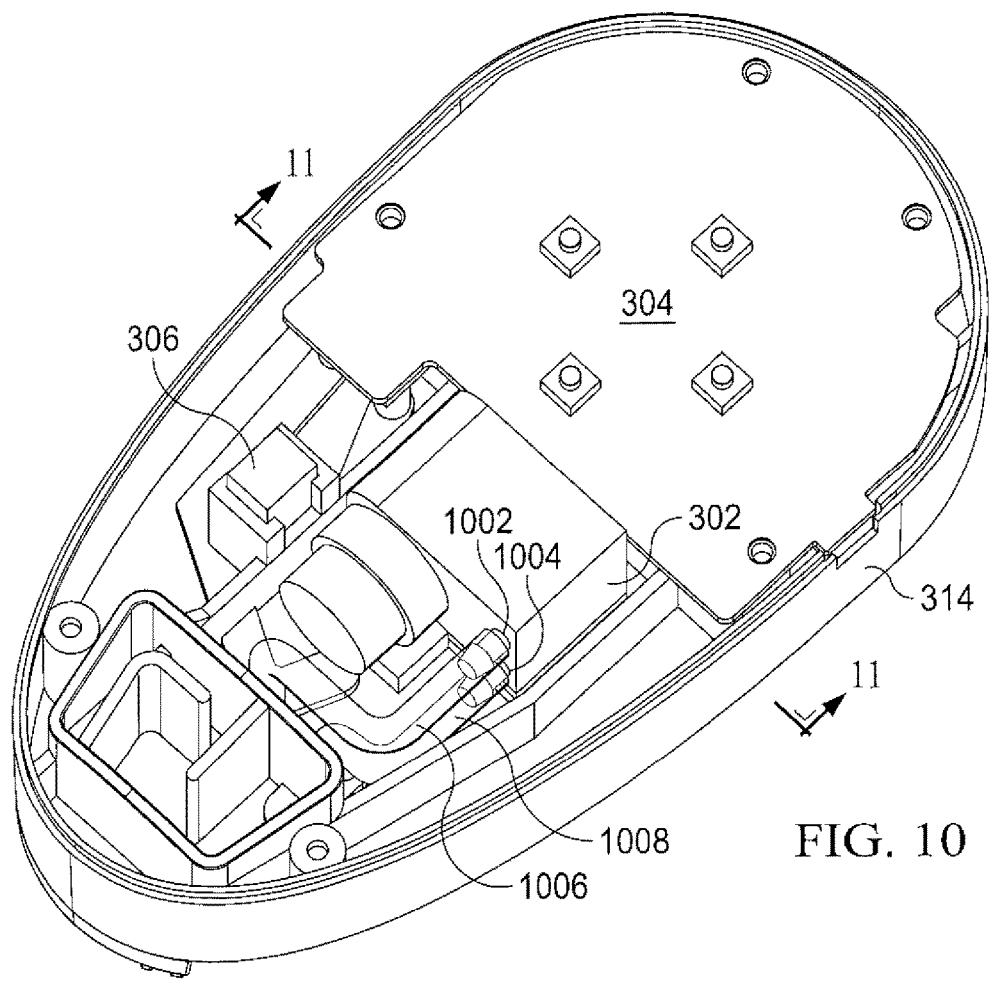
FIG. 10 is a perspective view of the housing of FIG. 3 partially assembled.

FIG. 10 is a perspective view of the second housing 314 partially assembled with the vacuum pump 302, the printed wiring assembly 304, and the valve 306. The vacuum pump 302 may include a negative-pressure port 1002 and a positive-pressure port 1004. For example, the vacuum pump 302 may produce a vacuum at the negative-pressure port 1002 and exhaust fluid under positive pressure at the positive-pressure port 1004. The negative-pressure port 1002 may be fluidly coupled to the fluid channel 404a, and the positive-pressure port 1004 may be fluidly coupled to the fluid channel 404c. For example, a tube 1006 may fluidly couple the negative-pressure port 1002 to the fluid channel 404a through the channel port 610, and a tube 1008 may fluidly couple the positive-pressure port 1004 to the fluid channel 404c through the channel port 616.

Figure 11:
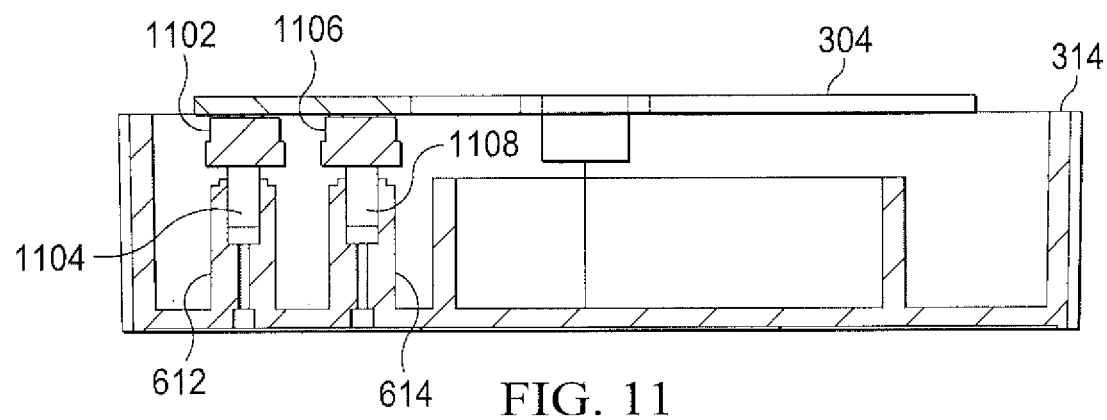
FIG. 11 is a section view of the assembly of FIG. 10 taken along line 11-11.

FIG. 11 is a section view of the assembly of FIG. 10 taken along line 11-11, illustrating additional details that may be associated with some embodiments. For example, FIG. 11 illustrates an interface between the printed wiring assembly 304 and the channel ports 612 and 614. In the example embodiment of FIG. 11, the printed wiring assembly 304 may include pneumatic sensors, such as a pressure transducer 1102 having a transducer port 1104 and a second pressure transducer 1106 having a transducer port 1108. In some embodiments, the transducer port 1104 may be inserted into the channel port 612 and the transducer port 1108 may be inserted into the channel port 614, as illustrated in the example of FIG. 11. Although only two connections are illustrated in the section view of FIG. 11, similar principles may be readily applied to connect other components, such as the pump 302.

Figure 12:
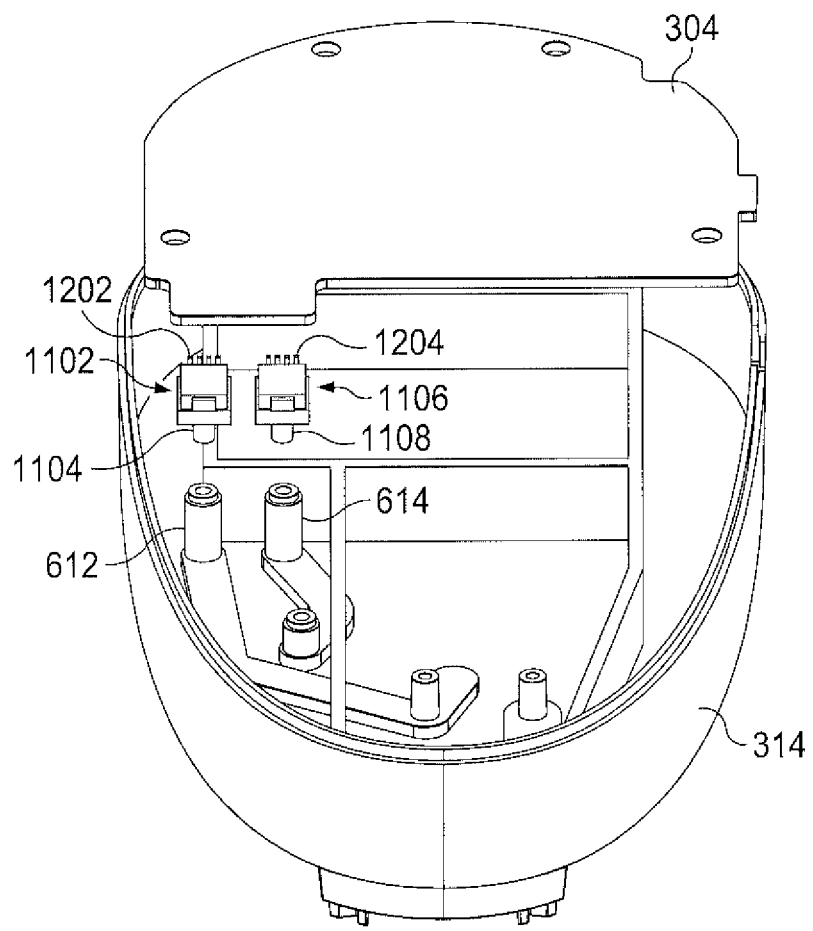
FIG. 12 is an exploded view of FIG. 10.

FIG. 12 is an exploded view of FIG. 10, illustrating additional details that may be associated with some embodiments. For example, FIG. 12 further illustrates the pressure transducer 1102 and the pressure transducer 1106. The transducer port 1104 may be configured to be press-fit into the channel port 612, for example, and the transducer port 1108 may be similarly configured to be press-fit into the channel port 614. The pressure transducer 1102 may also comprise electrical conductors, such as conductive pins 1202, configured to be coupled to a compatible port (not shown in FIG. 12) on the printed wiring assembly 304. The pressure transducer 1106 may include similar or analogous pins 1204.

Figure 13:
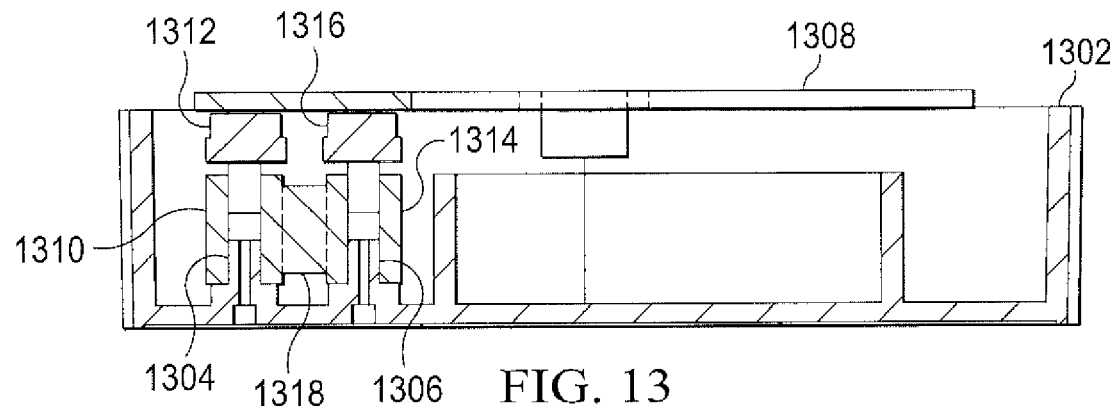
FIG. 13 is a section view of another example embodiment of a fluid coupling between two components.

FIG. 13 is a section view of another example embodiment of a fluid coupling between two components. FIG. 13 illustrates a housing 1302, a channel port 1304, a channel port 1306, and a printed wiring assembly 1308, which may be similar or analogous to the second housing 314, the channel port 612, the channel port 614, and the printed wiring assembly 304, respectively. In the example embodiment of FIG. 13, a first fitting 1310 can join the channel port 1304 to a pneumatic component of the printed wiring assembly 1308, such as a first pressure transducer 1312. A second fitting 1314 can join the channel port 1306 to another pneumatic component, such as a second pressure transducer 1316. Fittings such as the first fitting 1310 and the second fitting 1314 may be constructed from a thermoplastic elastomer or similar flexible material, which can provide an interference fit between the fittings and respective pneumatic components. In some embodiments, a yoke 1318 can join the first fitting 1310 and the second fitting 1314, which can be fabricated as a single unit. Fittings may also be over-molded as part of the housing 1302 in some embodiments, but in other embodiments fittings may be fabricated separately and press-fit onto the housing 1302. Although only two fittings are illustrated in the section view of FIG. 13, similar principles may be readily applied to connect other components, and more than two fittings may be fabricated as a single unit similar or analogous to the fittings illustrated in FIG. 13.

Figure 14:
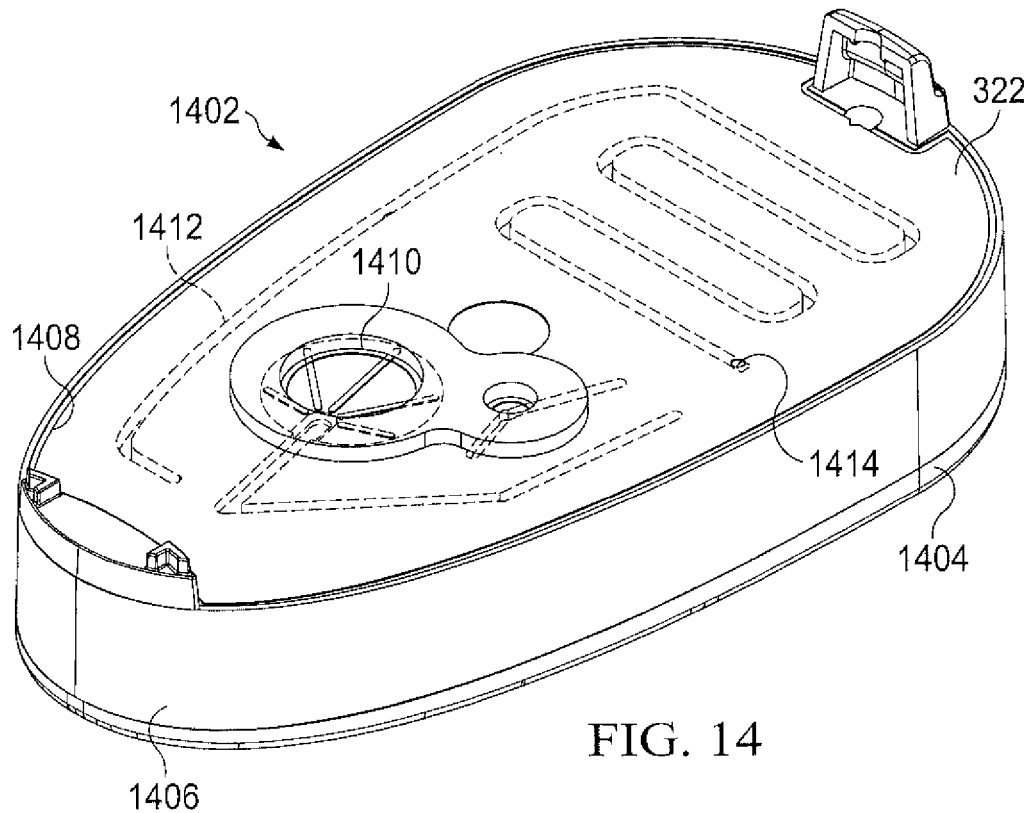
FIG. 14 is a perspective view of another example of a housing that may be associated with some embodiments of a control unit.

FIG. 14 is a perspective view of another example of a housing 1402 that may be associated with some embodiments of a control unit, such as the control unit 200 of FIG. 2. The housing 1402 may be similar or analogous to the housing 202, and may include any combination of the features of the housing 202. For example, the housing 1402 may have a first housing 1404, a second housing 1406, and a panel 1408 with integrated fluid channels, analogous to the first housing 312, the second housing 314, and the panel 402, respectively. FIG. 14 illustrates the first housing 1404 assembled with the second housing 1406, and the seal 322 secured to the panel 1408. A canister port 1410 may also be coupled the panel 1408. For example, as shown in the example embodiment of FIG. 14, the canister port 1410 may be integral to the panel 1408, and may also be fluidly coupled to one or more of the fluid channels. In the example embodiment of FIG. 14, a fluid channel 1412 may be fluidly coupled to an exhaust port of a vacuum pump (not shown in FIG. 14). In some embodiments, the fluid channel 1412 may be curved or serpentine to increase the length of the fluid channel 1412, analogous to the baffles 307, which can effectively reduce pressure peaks and sound level of exhaust flow. The diameter of the fluid channel 1412 can also be adjusted in some embodiments to reduce the sound level. Fluid may be vented through an aperture 1414 in the seal 322 over the fluid channel 1412, preferably at a downstream extremity of the fluid channel 1412.

Figure 15:
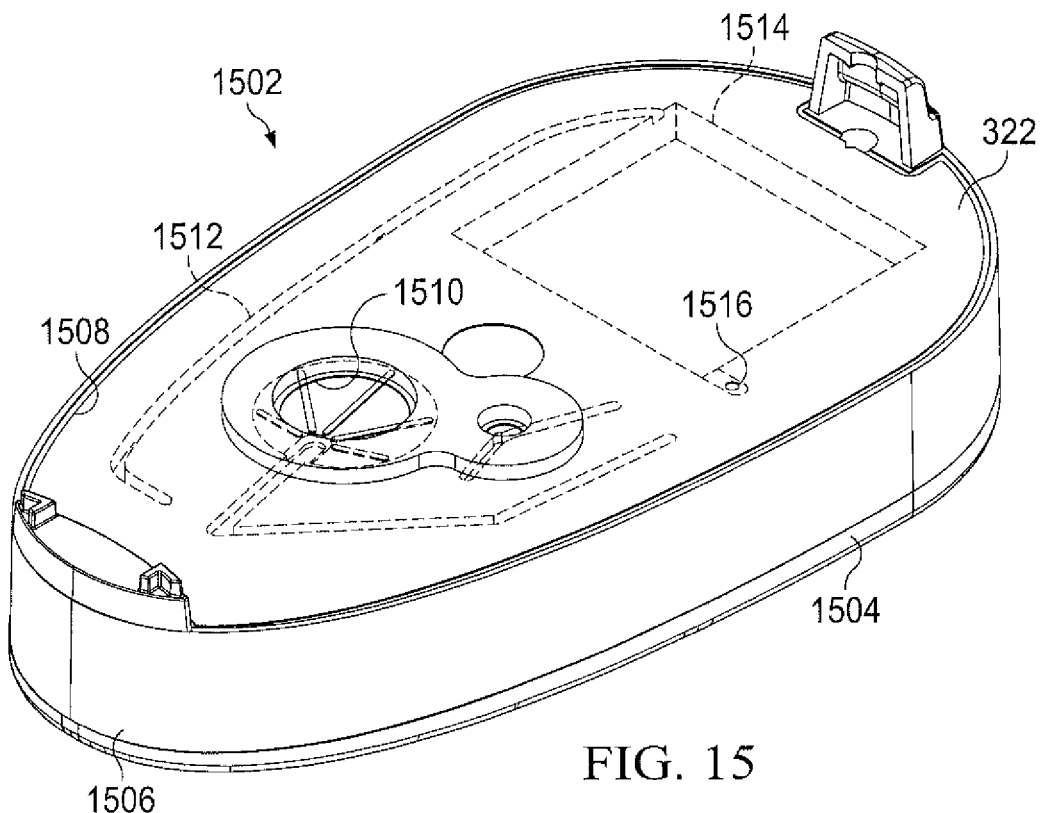
FIG. 15 is a perspective view of another embodiment of a housing that may be associated with some embodiments of a control unit.

FIG. 15 is a perspective view of another embodiment of a housing 1502 that may be associated with some embodiments of a control unit, such as the control unit 200. The housing 1502 may be similar or analogous to the housing 202, and may include any combination of the features of the housing 202. For example, the housing 1502 may have a first housing 1504, a second housing 1506, and a panel 1508 with integrated fluid channels, analogous to the first housing 312, the second housing 314, and the panel 402, respectively. FIG. 15 illustrates the first housing 1504 assembled to the second housing 1506, and the seal 322 secured to the panel 1508. A canister port 1510 may also be coupled the housing 1502. For example, as shown in the example embodiment of FIG. 15, the canister port 1510 may be integral to the panel 1508, and may also be fluidly coupled to one or more of the fluid channels. In the example embodiment of FIG. 15, the fluid channel 1512 may be fluidly coupled to an exhaust port of a vacuum pump (not shown in FIG. 15). The fluid channel 1512 may also be fluidly coupled to the expansion chamber 1514, analogous to the expansion chamber 324. In the example embodiment of FIG. 15, the expansion chamber 1514 is an open chamber. The fluid capacity of the expansion chamber 1514 is preferably sufficiently large to dissipate exhaust pressure delivered through the fluid channel 1512. In some embodiments, the expansion chamber 1514 may also include baffles or sound-absorbing foam to further reduce sound produced by exhaust flow from a vacuum pump. Fluid may be vented through an aperture 1516 in the seal 322 over the expansion chamber 1514.

Figure 16:
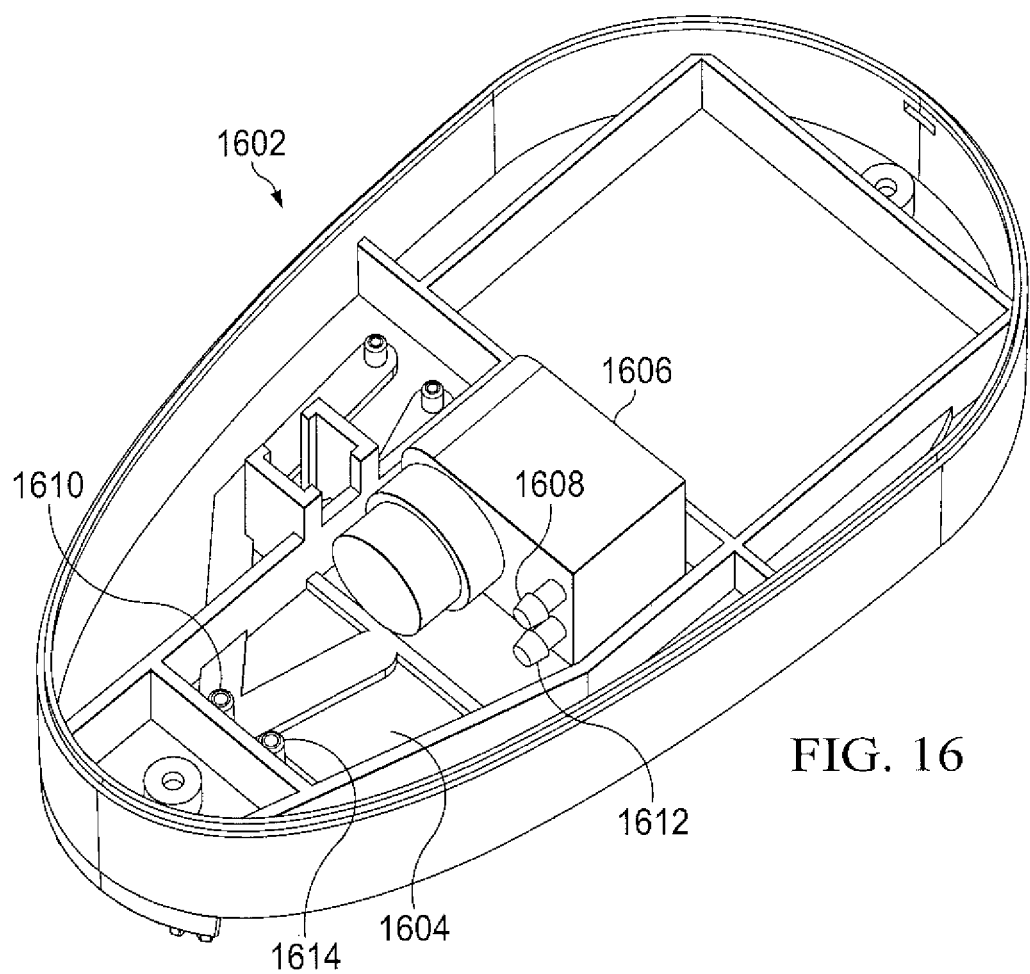
FIG. 16 is a perspective view of yet another example of a housing that may be associated with some embodiments of a control unit.

FIG. 16 is a perspective view of yet another example of a housing 1602 that may be associated with some embodiments of a control unit, such as the control unit 200. The housing 1602 may be similar or analogous to the second housing 314, and may include any combination of the features of the second housing 314. In the example embodiment of FIG. 16, the housing 1602 may include a pump chamber 1604, analogous to the pump compartment 606 in the example embodiment of FIG. 6. A vacuum pump 1606 may be disposed in the pump chamber 1604. The vacuum pump 1606 may include a vacuum port 1608, which may be fluidly coupled through a tube or other fluid conductor (not shown in FIG. 16) to a fluid port 1610 to deliver negative-pressure to other components. Positive-pressure fluid may be exhausted from the vacuum pump 1606 through an exhaust port 1612 directly into the pump chamber 1604, and then vented through an aperture 1614 in the housing 1602. Exhausting fluid directly into the pump chamber 1604 can reduce the number of fluid connections in some embodiments.

Figure 17:
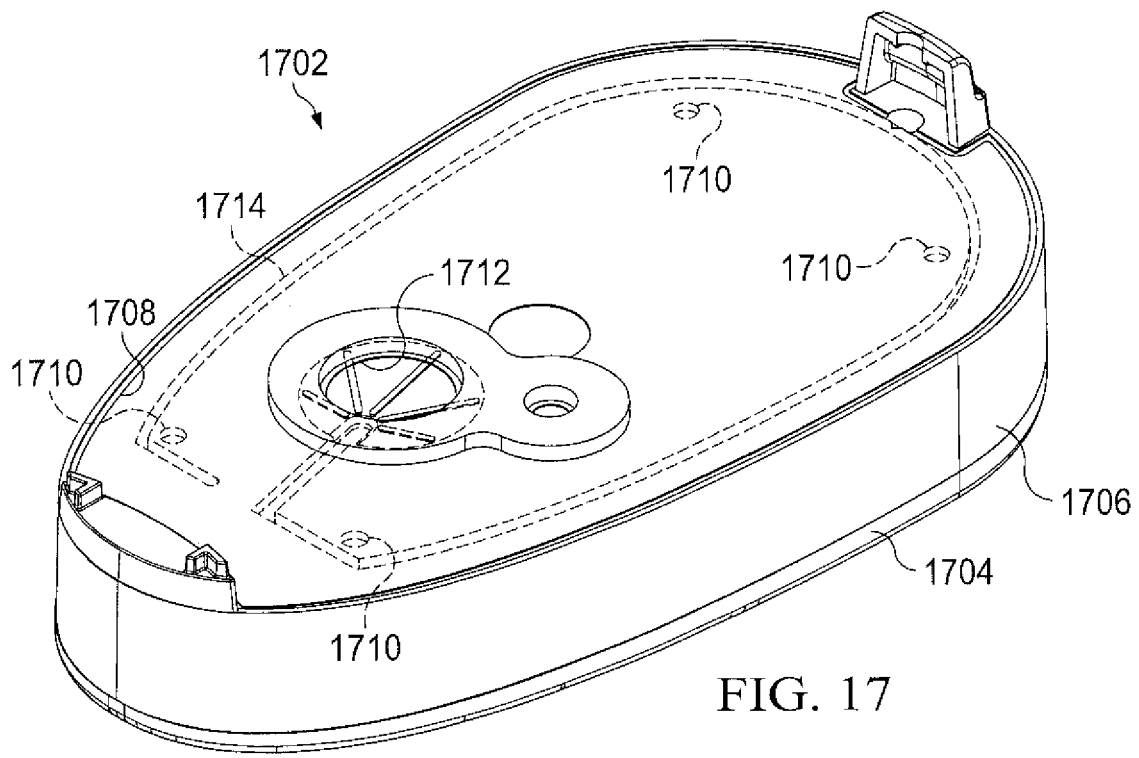
FIG. 17 is a perspective view of another example embodiment of a housing that may be associated with a control unit.

FIG. 17 is a perspective view of another example embodiment of a housing 1702 that may be associated with a control unit, such as the control unit 200. The housing 1702 may be similar or analogous to the housing 202, and may include any combination of the features of the housing 202. For example, the housing 1702 may have a first housing 1704, a second housing 1706, and a panel 1708 with integrated fluid channels, analogous to the first housing 312, the second housing 314, and the panel 402, respectively. FIG. 17 illustrates the first housing 1704 assembled with the second housing 1706, and the seal 322 secured to the panel 1708. Fasteners (not visible in FIG. 17) may be inserted through holes 1710 in the panel 1708 to secure the first housing 1704 to the second housing 1706. Suitable fasteners may include screws, clips, or pins, for example. The housing 1702 may also have a canister port 1712. The seal 322 and a fluid channel 1714 can provide an integrated fluid conductor between a negative-pressure source (not shown) and the canister port 1712. In the example embodiment of FIG. 17, a substantial portion of the fluid channel 1714 tracks a perimeter of the panel 1708. In some applications, it may be important to prevent tampering with the housing 1702 for safety or reliability. Accordingly, in some embodiments, the holes 1710 may be disposed in the panel 1704 interior to the fluid channel 1714, so that an attempt to remove the seal 322 to remove the fasteners may create a leak in the fluid conductor between a negative-pressure source and the canister port 1712. Such a leak can effectively prevent application of negative-pressure therapy in some embodiments, or an appropriate alarm may be generated upon detecting such a leak.

In operation, the control unit 200 may be coupled to a canister, such as the container 112 of FIG. 1, which can be fluidly coupled to a dressing, such as the dressing 102 of FIG. 1. The vacuum pump 302 can produce a prescribed negative pressure, which can be distributed to the canister through the canister port 406. The negative pressure can then be distributed through the canister to the dressing.

Many negative-pressure therapy systems may use a reciprocating diaphragm or piston pump to generate negative pressure for therapy. For example, the vacuum pump 302 may be a reciprocating pump. In operation, this type of pump typically emits exhaust pulses, which can be a significant source of noise. Noise can be particularly problematic in smaller pumps that produce relatively high airflow rates, since smaller pumps generally rotate at a higher speed to produce higher flow rates. Excessive noise can interfere with patient compliance, particularly in public places or at night.

In some embodiments, a plenum or extended exhaust pathway, such as illustrated by the expansion chamber 324, the fluid channel 1412, or the expansion chamber 1514, can reduce pressure peaks of exhaust flow, reducing the sound level of an apparatus without significantly increase the size or cost of an apparatus. Baffles, sound-absorbing foam, or both may additionally or alternatively be used to reduce the sound level. For example, exhaust air from the positive-pressure port 1004 of the vacuum pump 302 may enter the expansion chamber 324 through the channel port 616, Within the expansion chamber 324, sound waves may be reflected and interfere with each other, which can significantly reduce the sound level, before leaving the expansion chamber 324 through an aperture in the panel 402, The mounting foam 310, which can seal the expansion chamber 324 in some embodiments, can also absorb sound waves to further reduce the sound level of an apparatus.

The systems, apparatuses, and methods described herein may provide significant advantages, For example, in some embodiments, the housing 202 can eliminate undercuts so that it can be molded with open-and-shut tooling, which can be significantly less expensive than other manufacturing processes. Fluid channels may also be integrated into an outer surface of the housing 202 to make desired fluid connections between components, which can significantly reduce the number of parts in a system, Reducing the number of parts can also reduce the cost and complexity of manufacturing. Moreover, reducing the use of ancillary tubing can also reduce the risk of connections blocked by twisted or bent tubes. To further reduce the amount of tubing required, some embodiments can combine integrated fluid channels with a custom fitting configured to make multiple fluid connections.

While shown in a few illustrative embodiments, a person having ordinary skill in the art will recognize that the systems, apparatuses, and methods described herein are susceptible to various changes and modifications. In particular, particular features may be emphasized in some example embodiments while being omitted in others, but a person of skill in the art will appreciate that features described in the context of one example embodiment may be readily applicable to other example embodiments. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for providing negative-pressure therapy, the apparatus comprising:
   a first housing;
   a second housing configured to be coupled to the first housing;
   a panel having an inner surface and an outer surface, the inner surface facing the first housing, the panel coupled to the second housing;
   a first fluid channel integrated into the outer surface of the panel;
   a second fluid channel integrated into the outer surface of the panel;
   a first channel port integrated into the panel and fluidly coupled to the first fluid channel;
   a second channel port integrated into the panel and fluidly coupled to the second fluid channel;
   a pump disposed between the first housing and the second housing, the pump comprising a negative-pressure port fluidly coupled to the first channel port and a positive-pressure port fluidly coupled to the second channel port;

a canister port coupled to the panel and fluidly coupled to the first fluid channel upstream of the negative-pressure port;

an expansion chamber coupled to the panel and fluidly coupled to the second fluid channel downstream of the positive-pressure port; and an adhesive label coupled to the panel over the first fluid channel and the second fluid channel.

2. The apparatus of claim 1, wherein the panel, the first fluid channel, the first channel port, the second fluid channel, the second channel port, the canister port, and the expansion chamber consist of surfaces having a positive parting angle in at least one orientation.

3. The apparatus of claim 1, further comprising a fluid container fluidly coupled to the canister port.

4. The apparatus of claim 1, further comprising:

a fluid container fluidly coupled to the canister port; and a dressing fluidly coupled to the fluid container.

\* \* \* \* \*